United States Patent

Sekiguchi et al.

[11] Patent Number: 5,821,407
[45] Date of Patent: Oct. 13, 1998

[54] AUTOMATIC VISCOSITY MEASURING APPARATUS WITH ROTOR AUTOMATICALLY DETACHABLE

[75] Inventors: Koji Sekiguchi, Komae; Yoshihiko Shimoda, Yokohama, both of Japan

[73] Assignee: Toki Sangyo Co., Ltd., Japan

[21] Appl. No.: 637,643

[22] PCT Filed: Jul. 27, 1994

[86] PCT No.: PCT/JP94/01237

§ 371 Date: Mar. 29, 1996

§ 102(e) Date: Mar. 29, 1996

[87] PCT Pub. No.: WO95/09353

PCT Pub. Date: Apr. 6, 1995

[30] Foreign Application Priority Data

Sep. 29, 1993 [JP] Japan ................................ 5-243177

[51] Int. Cl.⁶ .................................................. G01N 11/14
[52] U.S. Cl. ........................ 73/54.28; 73/54.35; 483/58; 483/27; 279/128
[58] Field of Search ................ 73/54.23, 54.24, 73/54.25, 54.26, 54.27, 54.28, 54.29, 54.31, 54.3, 54.33, 54.34, 54.35, 54.38; 279/128; 483/58, 59, 20, 22, 27

[56] References Cited

U.S. PATENT DOCUMENTS

| | | |
|---|---|---|
| 2,812,203 | 11/1957 | Scholten ............................ 279/128 X |
| 4,649,623 | 3/1987 | Schneider et al. ................. 279/128 X |
| 4,761,877 | 8/1988 | Rupp ..................................... 483/59 X |
| 5,041,806 | 8/1991 | Enderle et al. ......................... 335/295 |

FOREIGN PATENT DOCUMENTS

| | | |
|---|---|---|
| A-63-74574 | 4/1988 | Japan . |
| A-2-231549 | 9/1990 | Japan . |
| A-2-251758 | 10/1990 | Japan . |
| A-2-251764 | 10/1990 | Japan . |
| A-2-167448 | 7/1991 | Japan . |

*Primary Examiner*—Michael Brock
*Attorney, Agent, or Firm*—Pennie & Edmonds LLP

[57] ABSTRACT

An off-line automatic viscosity measuring apparatus, which can execute viscosity measurement of a plurality of specimens while automatically replacing rotors, is provided. The off-line automatic viscosity measuring apparatus according to the invention has: a detachable rotor 7; a viscosity detection head 33 for executing viscosity measurement with the rotor 7 connected thereto; a detection head moving mechanism 34 for moving the viscosity detection head 33 up and down and left and right; a separation aid mechanism 50 for aiding in separation of the rotor 7 and the viscosity detection head 33; and a rotor magazine mechanism 40 for holding a plurality of rotors 7. The viscosity detection head 33 has a bottom end formed with a detection head attaching/detaching part for accepting the rotor 7. The rotor 7 has a top end formed with a rotor side attaching/detaching part being inserted into the detection head attaching/detaching part for connecting the rotor 7 and the viscosity detection head 33.

12 Claims, 16 Drawing Sheets

AUTOMATIC VISCOSITY MEASURING APPARATUS WITH ROTOR AUTOMATICALLY DETACHABLE

TECHNICAL FIELD

This invention relates to a rotary viscometer for measuring the viscosity of a liquid specimen and in particular to an automatic rotor attaching/detaching mechanism applied to an off-line automatic viscosity measuring apparatus for automatically measuring a plurality of specimens.

TECHNICAL BACKGROUND

In almost all industrial fields for handling raw material and products in liquid form, such as paint, ink, and semiconductor industries including petrochemical, synthetic chemical engineering, drug, and food industries, the viscosity of liquids is measured, thereby determining whether or not the raw material is suitable, whether the process is proper, and whether the products are good. Such viscosity measurement is mainly intended for quality control as to whether or not the material, intermediate products, and final products are proper in quality.

To inspect intermediate or final products in such various industrial fields, so-called off-line measurement is widely executed wherein specimens provided by sampling the liquids in vessels such as beakers are collected in an analysis chamber where various physical property values of the substances, such as the density, electrical conductivity, pH, and moisture content, are measured intensively. With recent advances in measuring instruments, it has become possible to automatically measure a large number of physical property values in the off-line measurement.

However, viscosity measurement cannot be automated because of the structure of a viscometer as described below and must depend on workers for manual measurement, leading to an obstacle to the reduction in inspection costs or measurement data management.

The reason why conventional rotary viscometers are not suitable for automation of off-line viscosity measurement is because of the structure of the viscosity detection part related to the measurement form. That is, when a detection head of the viscometer is mounted on a mechanical movement manipulation mechanism such as an industrial robot, and is run or moved up and down, the viscometer detection head cannot resist a mechanical shock applied thereto and easily suffers a breakdown. To prevent mutual contamination of liquids by sample liquids adhering to a rotor at the time of measurement, automatic cleaning or replacing of the rotor is required at each measurement. However, the mechanical structure of the conventional viscometer cannot endure an external force applied to the rotor during such an operation.

The structural problem as mentioned above is involved in the properties of the viscometer. That is, to measure the viscosity, the viscometer requires the inevitable function as a high-performance minute torque detector. To detect the minute torque, the bearing friction of a shaft support of a torque detection shaft needs to be small. However, to lower the bearing friction, it is necessary to use a shaft support mechanism comprising a jewel bearing and a pivot in combination as a low friction bearing and to make axial load applied to the jewel bearing as lightweight as possible.

For these reasons, the conventional viscometer must have shaft rotation parts with thin and small-diameter dimensions even at the expense of strength. Inevitably, the rigidity of the torque detection shaft peripheral mechanical portion becomes weak. Further, as is generally known, the bearing mechanism comprising a jewel bearing and a pivot in combination is extremely weak in terms of mechanical shock resistance; this part easily suffers breakdown and has been the Achilles' heel of the rotary viscometer.

To solve such a problem of the conventional rotary viscometer easily suffering a breakdown, the present inventor has filed the application "Rotary viscometer with automatic protector for protecting jewel bearing and pivot" (Japanese Patent Application No. Hei 1-51655 and Japanese Patent Laid-Open No. Hei 2-231549). This previous application is an invention relating to a rotary viscometer wherein a jewel bearing and pivot come in automatic contact with each other only at the time of viscosity measurement and a torque detection shaft is supported with the jewel bearing, the measurement mode being entered; at the time of nonmeasurement, rotor shaft rotation is automatically restrained at the same time as the jewel bearing and pivot are separated from each other, thereby automatically protecting the jewel bearing and pivot in association with running of the viscometer.

This previous invention has made it possible to apply the rotary viscometer to an off-line automatic viscosity measuring apparatus.

However, up to now, only several apparatus examples adopting the automatic rotor cleaning method have been embodied as examples of off-line automatic viscosity measuring apparatuses using the rotary viscometer with the automatic protector; full-scale off-line automatic viscosity measuring apparatuses are not provided. This is because the following important technique is not established:

Not only protection of the jewel bearing and pivot, but also a technique for preventing mutual contamination of liquids by specimen liquid adhering to the rotor is required to provide the off-line automatic viscosity measuring apparatus.

By the way, a single rotor is used for different types of measurement in the automatic rotor cleaning method. Thus, this method is effective only when a plurality of specimen liquids have a similarity in viscosity characteristic and can be measured with the same-shaped rotor; it is not effective when the specimen liquids differ in viscosity characteristic and cannot be measured with the same-shaped rotor.

This means that it is indispensable to establish an automatic replacement technique of rotors compliant with a wider range of conditions in addition to automatic rotor cleaning for automatic measurement of a wider range of types of specimen liquids.

One of a few examples of the automatic rotor replacement device in the related art is the application filed by the present inventor, "Automatic rotor attaching/detaching device for rotary viscometer" (Japanese Patent Application No. Hei 1-308017 and Japanese Patent Laid-Open No. Hei 3-167448) using a shape-memory alloy. The application will be outlined below as a related art to the present invention.

FIGS. 11 (a) and (b) are illustrations of the operation principles of the automatic rotor attaching/detaching device. This automatic rotor attaching/detaching device in the related art comprises a connector adapter 23 and a heater/cooler 24. In FIG. 11 (a), the connection adapter 23, which is threadably attached to a rotor shaft bottom end 15b, is made of a grip member 32 incorporating a central connection metal fixture 23a, a bias plate spring 23b shaped like a C letter, and a U-shaped plate spring 23c made of a unidirectional shape-memory alloy shaped into a predetermined form. The heater/cooler 24 comprises an air spray nozzle 24c containing a heater 24b.

The shape-memory alloy used with the plate spring 23c uses an alloy having an operation start temperature reasonably higher (about 20–30 degrees Celsius) than the measurement temperature of the specimen liquid whose viscosity is to be measured.

The operation of the automatic rotor attaching/detaching device is as follows:

To attach a rotor 7, hot air is blown onto the connection adapter 23 through the nozzle 24c in FIG. 11 (a) for raising the temperature in excess of the operation start point at which the plate spring 23c made of the shape-memory alloy starts operating. Then, the plate spring 23c is restored to the memorized original open shape, thus pushing open the C-shaped bias plate spring 23b, opening a bottom end claw 23e of the C-shaped plate spring.

In this state, the taper face of a tip 7a of a stem of the rotor 7 is inserted into a bottom face taper hole 23d of the connection metal fixture 23a, then cool air is blown through the nozzle 24c. Then, the U-shaped plate spring 23c of the shape-memory alloy is cooled to room temperature and loses elasticity. Thus, a press force of the bias plate spring 23b causes the tip of the claw 23c to engage a reverse taper part 7b of the rotor stem tip 7a, securely holding the rotor 7 axially aligned with the rotor shaft, as shown in FIG. 11 (b).

To detach the rotor 7, again hot air is blown through the nozzle 24c for opening the bottom end claw of the C-shaped bias plate spring 23b as described above, thereby automatically detaching and dropping the rotor 7.

Up to now, we have discussed the example in which the shape-memory alloy spring is a plate spring, but various forms such as coil springs rather than plate springs are possible as the shape-memory alloy springs.

However, since the apparatus using this kind of shape-memory alloy spring and heating and cooling it for operation uses a thermal phenomenon as the operation principle, the heater/cooler and its temperature control are required and the attaching/detaching operation speed is also slow.

As described above, in various industrial fields handling liquids, hitherto, viscosity measurement for quality inspection and process inspection at various stages of material, intermediate process, and products has been executed in an analysis chamber as off-line work by the manual operation of workers. This manual work, which is man-power work, causes not only human measurement errors, but also measurement operation mistakes if a large number of specimens are to be measured.

Further, for viscosity change measurement with time such as hardening time measurement of a 2-liquid adhesive, the worker must focus attention on the specimen and repeat manual measurement until the measurement is complete.

Thus, to rationalize the troublesome jobs, it has for some time been desired to use an off-line automatic viscosity measuring apparatus to intensively execute automatic measurement.

However, to provide such an automatic apparatus which did not exist in the past, it is first necessary to improve the conventional viscometer detection head easily suffering a breakdown in order to enhance reliability as a measuring instrument and secondly, to prevent mutual contamination of specimen liquids adhering to a rotor, a technique must be found that can be used more generally and widely independently of restrictions of solvents, etc., than automatic rotor cleaning.

That is, it is necessary to establish an automatic rotor replacement technique for measurement while replacing the current rotor with a new one for each specimen liquid to which viscosity measurement is applied, particularly a technique enabling rotor replacement in a short time.

The first one of the two problems can be completely solved by the automatic jewel bearing and pivot automatic protector working in association with the operation stop of the viscometer detection head as described above.

However, the second problem remains almost unsolved, and up to now only the method using the shape-memory alloy spring described above has been provided.

DISCLOSURE OF INVENTION

It is an object of the invention to provide a full-scale off-line automatic viscosity measuring apparatus and method by using a moving mechanism such as an industrial robot, for example, as an operation function working at an even higher speed to provide an automatic rotor attaching/detaching function associated with the motion of the moving mechanism, other than merely solving the second problem mentioned above, namely, the automatic rotor replacement technique, as a simple mechanical connection method problem of a viscosity detection head and a rotor.

It is another object of the invention to provide a rotary viscometer enabling automatic rotor replacement and a method enabling automatic rotor attaching and detaching.

The objects are accomplished by an automatic viscosity measuring apparatus comprising a detachable rotor and a detection head for measuring viscosity of a specimen liquid to be measured with the rotor connected thereto, wherein the improvement comprises: a detection head moving mechanism for moving the detection head between a connection position at which the rotor is connected to the detection head, a separation position at which the connected rotor is separated from the detection head, and a measurement position at which the viscosity of the specimen liquid is measured; a rotor holding section being disposed at the connection position for holding one or more rotors in a state in which they can be connected to the detection head; and a rotor move regulation section being disposed at the separation position for suppressing displacement of the rotor connected to the detection head when the rotor is separated; the rotor having a rotor side attaching/detaching part on a top end, the detection head having a detection head side attaching/detaching part on a bottom part, the rotor side attaching/detaching part and the detection head side attaching/detaching part each having a member on which an attraction force acts mutually.

The objects are also accomplished by a rotary viscometer comprising a detachable rotor and a detection head for measuring viscosity with the rotor connected thereto, wherein the improvement comprises: a detection head elevating mechanism for moving the detection head between a connection position at which the rotor is connected to the detection head, a separation position at which the connected rotor is separated from the detection head, and a predetermined initial position; a rotor holding section being disposed at the connection position for holding one or more rotors in a state in which they can be connected to the detection head; and a rotor movement regulation section being disposed at the separation position for suppressing displacement of the rotor connected to the detection head when the rotor is separated, the rotor having a rotor side attaching/detaching part on a top end, the detection head having a detection head side attaching/detaching part on a bottom part, the rotor side attaching/detaching part and the detection head side attaching/detaching part each having a member on which an attraction force acts mutually.

The objects are also accomplished by an automatic rotor attaching/detaching method used with a rotary viscometer comprising a detachable rotor and a detection head for measuring viscosity with the rotor connected thereto, the method comprising the steps of providing a rotor side attaching/detaching part disposed on a top end of the rotor and a detection head side attaching/detaching part disposed on a bottom end of the detection head, the rotor side and detection head side attaching/detaching parts each having a member on which an attraction force acts mutually, making one of the rotor side attaching/detaching part and the detection head side attaching/detaching part approach the other along a direction in which axial directions of both the parts substantially match for connecting both the attaching/detaching parts by the attraction force, thereby connecting the rotor and the detection head, and suppressing displacement of one of the rotor side attaching/detaching part and the detection head side attaching/detaching part in the direction and displacing the other along the direction against the attraction force for separating both the attaching/detaching parts, thereby separating the rotor and the detection head.

The objects are also accomplished by an automatic viscosity measurement method of a automatic viscosity measuring apparatus comprising a detachable rotor and a detection head for measuring viscosity with the rotor connected thereto, the method comprising the steps of providing a rotor side attaching/detaching part disposed on a top end of the rotor and a detection head side attaching/detaching part disposed on a bottom end of the detection head, the rotor side and detection head side attaching/detaching parts each having a member on which an attraction force acts mutually, moving the detection head to one of previously stored rotors, positioned at a predetermined connection position for making them approach each other along an axial direction in which both axial directions of the rotor and the detection head substantially match for connecting both the attaching/detaching parts by the attraction force, thereby connecting the rotor and the detection head, moving the detection head to which the rotor is connected to a predetermined viscosity measurement position and measuring viscosity, after the viscosity measurement is complete, moving the detection head with the rotor connected thereto to a predetermined separation position, and displacing said detection head in the axial direction against the attraction force with displacement of said rotor suppressed in the axial direction for separating both said attaching/detaching parts, thereby separating said rotor and said detection head.

As a method whereby a rotor can be attached or detached in a short time, the invention adopts a method wherein the attaching/detaching parts on which an attraction force, such as a magnetic attraction force, acts mutually are disposed in the detection head and rotor and the attraction force is used to connect the rotor to the detection head.

That is, in the automatic viscosity measuring apparatus comprising the detachable rotor and the detection head for measuring viscosity with the rotor connected thereto according to the invention, the rotor side attaching/detaching part is disposed on the top end of the rotor and the detection head side attaching/detaching part is disposed on the bottom end of the detection head for causing the attraction force to act on the rotor side attaching/detaching part and the detection head side attaching/detaching part mutually.

To connect the rotor and the detection head, one of the rotor side attaching/detaching part and the detection head side attaching/detaching part is made to approach the other along the direction in which their axial directions match and both the attaching/detaching parts are connected and fixed by the attraction force acting on both the attaching/detaching parts. To separate the rotor and the rotor shaft, one of the rotor side attaching/detaching part and the detection head side attaching/detaching part is fixed and the other is moved along the direction opposite to the connection direction against the attraction force, thereby separating both the attaching/detaching parts.

BRIEF DESCRIPTION OF THE DRAWINGS

FIG. 3 (b) is a partially sectional view when the example of the rotor magazine structure is viewed from the side.

FIG. 6 (b) is an illustration showing the positional relationship between a fork and a rotor in the attaching/detaching system in FIG. 6 (a).

FIG. 11 (b) is a partially sectional view showing a state in which a rotor is attached to the conventional automatic rotor attaching/detaching mechanism.

BEST MODE FOR CARRYING OUT THE INVENTION

Figure 1:
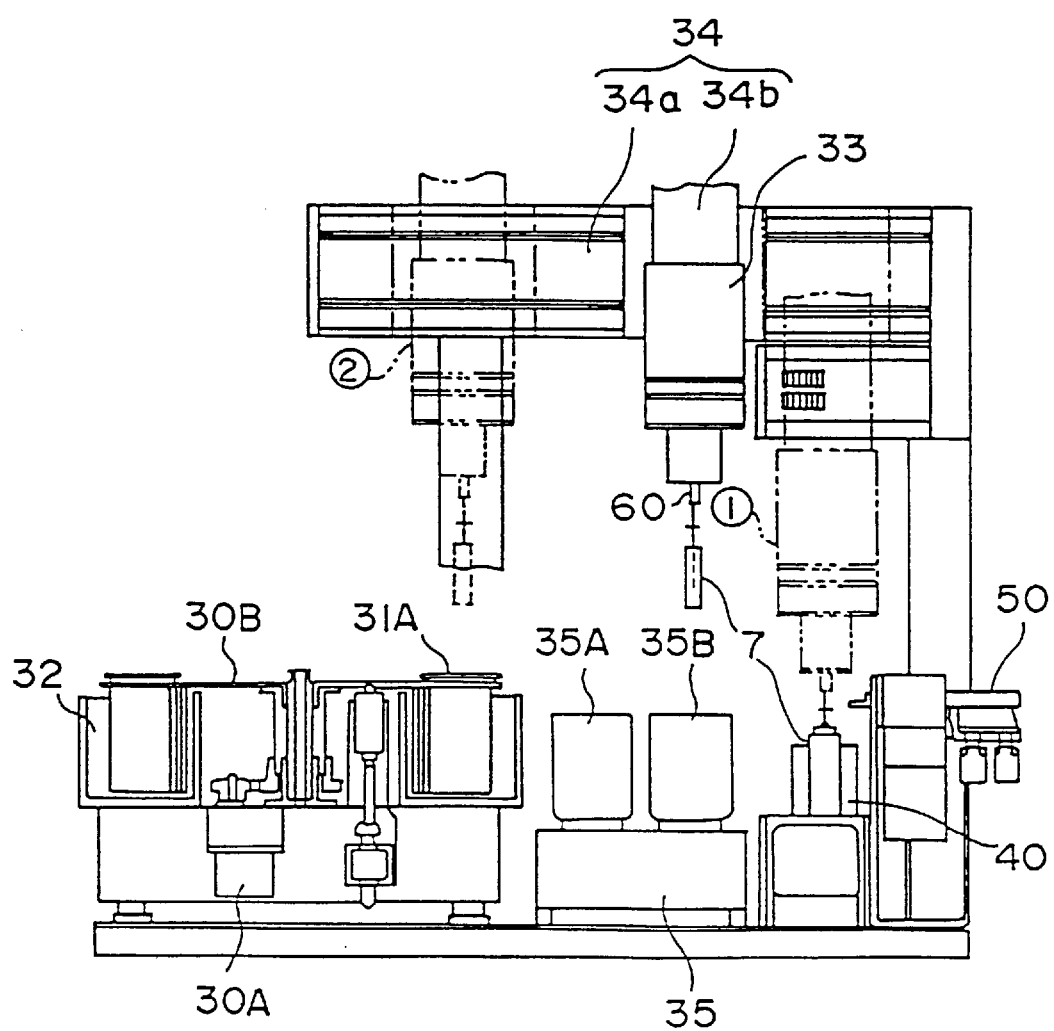
FIG. 1 is a front view of one embodiment of an automatic viscosity measuring apparatus to which the invention is applied.

An embodiment of an off-line automatic viscosity measuring apparatus with a turn table enabling automatic rotor attaching and detaching to which the invention is applied will be discussed with reference to FIGS. 1 to 10. In the description to follow, identical parts are denoted by the same reference numerals in the figures.

First, the configuration of the embodiment will be discussed.

Figure 2:
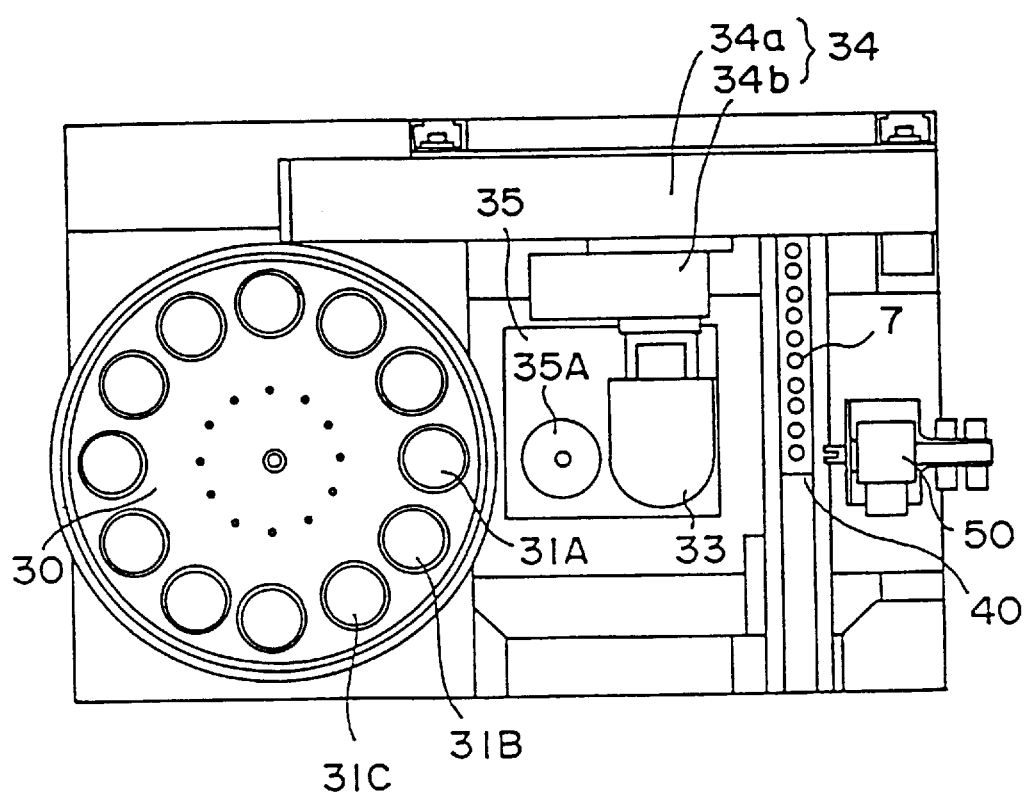
FIG. 2 is a top view of the embodiment in FIG. 1.
Figure 7A:
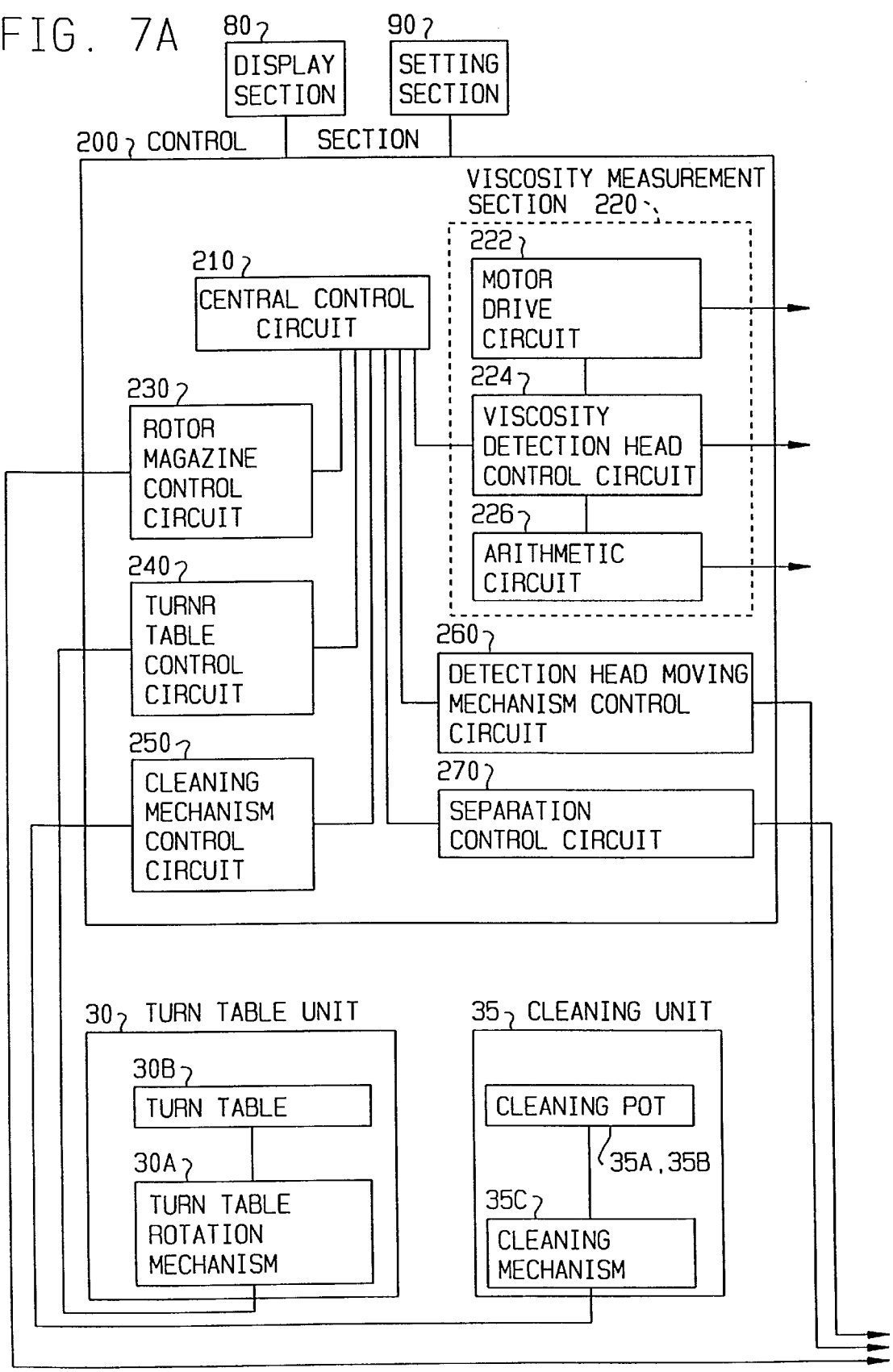
FIG. 7 is a block diagram showing the configuration of the embodiment to which the invention is applied.
Figure 7B:
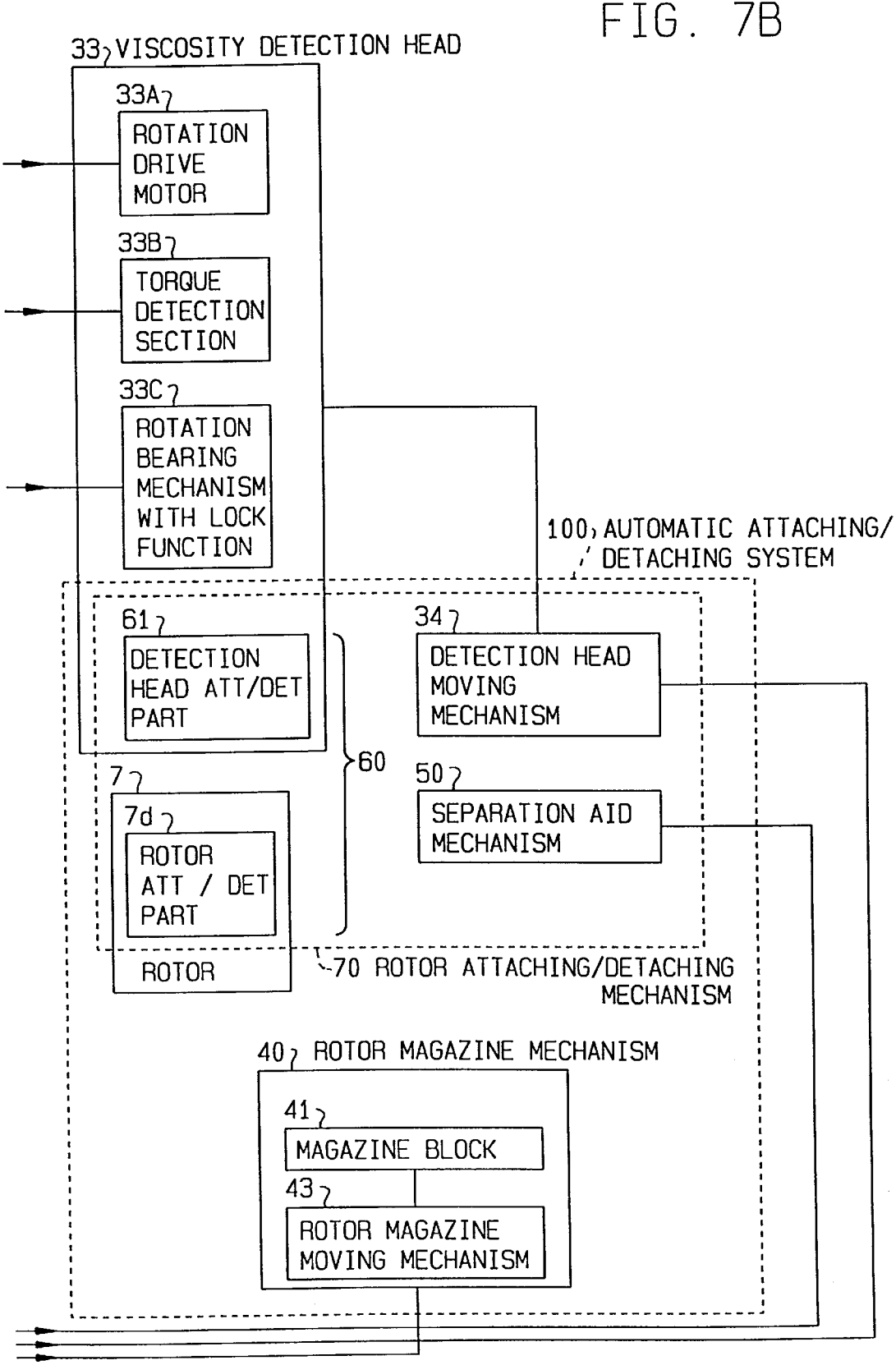

As shown in FIGS. 1, 2, and 7, the off-line automatic viscosity measuring apparatus according to the embodiment has a detachable rotor 7, a viscosity detection head 33 for executing viscosity measurement with the rotor 7 connected thereto, a detection head moving mechanism 34 for moving the viscosity detection head 33 up and down and left and right, and a separation aid mechanism 50 for aiding in separation of the rotor 7 and the viscosity detection head 33.

The viscosity detection head 33 has a bottom end formed with a detection head attaching/detaching part 61 for accepting the rotor 7. The rotor 7 has a top end formed with a rotor attaching/detaching part 7d being inserted into the detection head attaching/detaching part 61 for connecting the rotor 7 and the viscosity detection head 33.

The detection head moving mechanism 34 has a horizontal movement actuator 34a for horizontally moving the detection head 33, used with an industrial robot, etc., and a vertical elevating actuator 34b for vertically moving the detection head 33.

In the embodiment, the rotor attaching/detaching part 7d is inserted into the detection head attaching/detaching part 61 and restrained, whereby an attaching/detaching section 60 is formed and the viscosity detection head 33 and the rotor 7 are connected. An automatic rotor attaching/detaching function according to the invention can be provided by a rotor attaching/detaching mechanism 70 made up of the connection part 60, the detection head move mechanism 34, and the separation aid mechanism 50.

The embodiment further includes a rotor magazine mechanism 40 for holding a plurality of rotors 7. This rotor magazine mechanism 40 and the rotor attaching/detaching mechanism 70 make up an automatic attaching/detaching system 100 which can select one of the rotors 7 as desired for automatic rotor replacement.

The embodiment further includes an index turn table unit 30 for holding a plurality of beakers in which specimens to be measured are entered, a cleaning unit 35 for cleaning the rotors 7, a display section 80 for displaying the measurement results, etc., a setting section 90 for setting a measurement sequence, etc., and a control section 200 for controlling the operation of the components such as the viscosity detection head 33 and the detection head move mechanism 34 and calculating the viscosity of each specimen.

Figure 5:
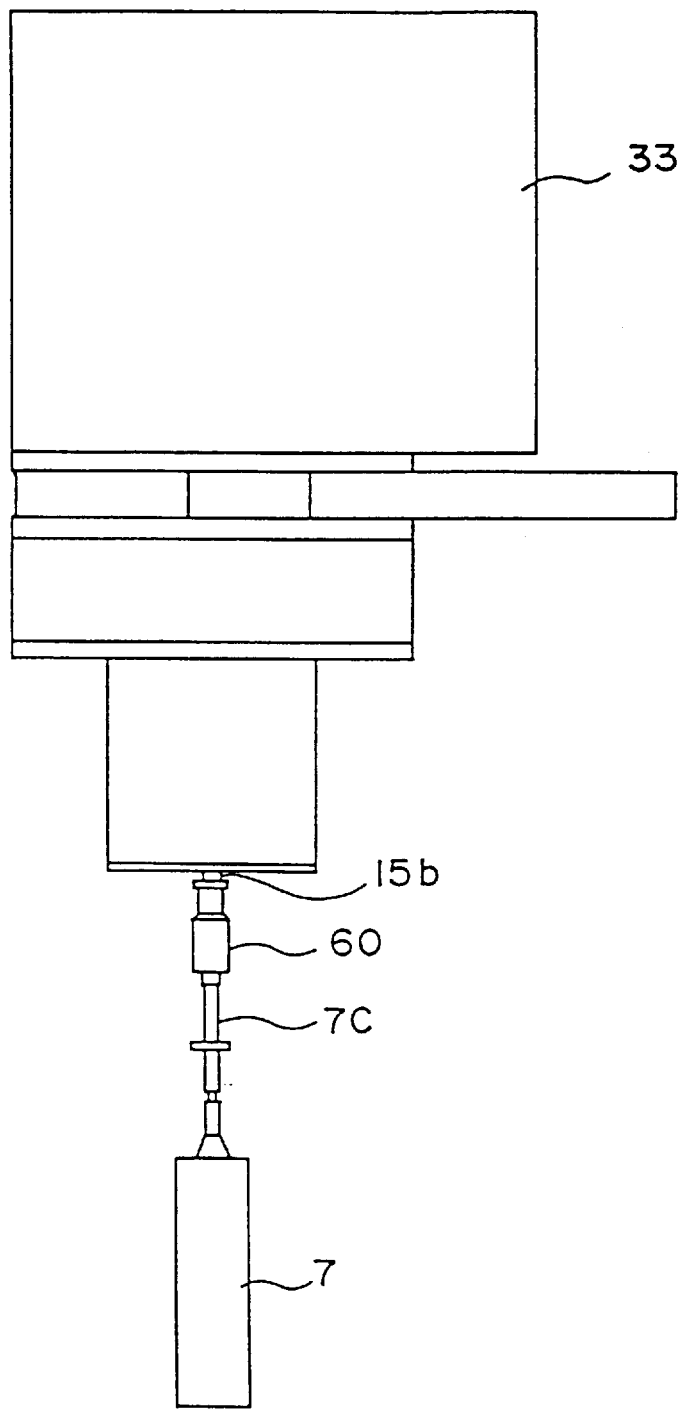
FIG. 5 is an illustration showing a state in which a viscosity detection head and a rotor are connected.
Figure 8:
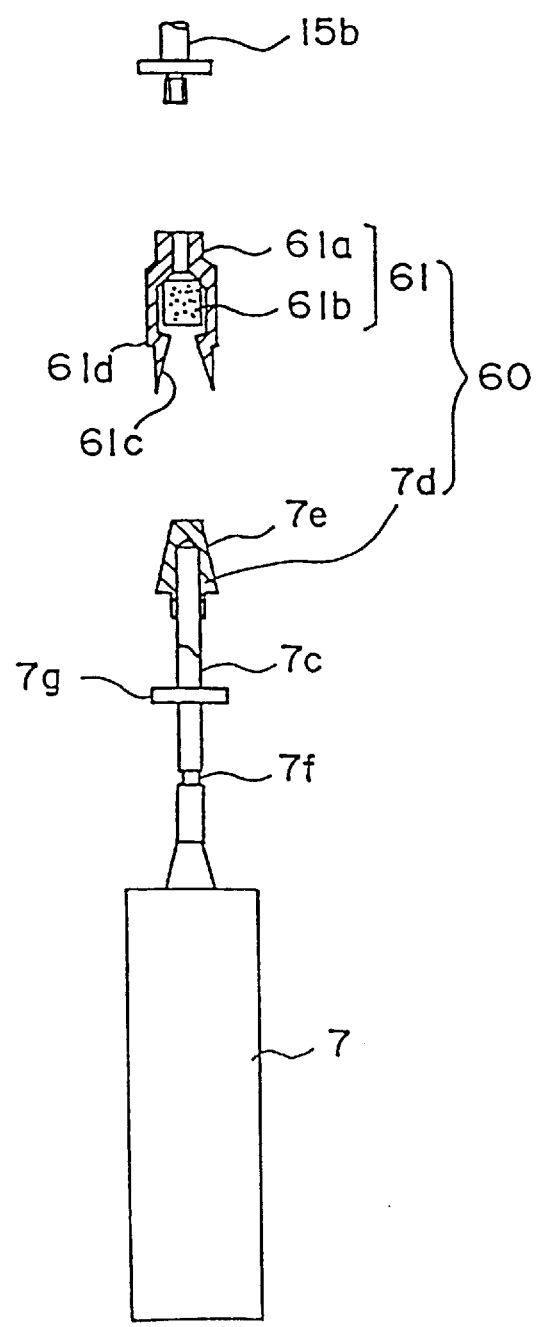
FIG. 8 is a partially sectional view showing the exploded structure of a rotor attaching/detaching part to which the invention is applied.

As shown in FIGS. 5 and 8, the attaching/detaching section 60 consists of the detection head attaching/detaching part, which will be hereinafter called a connection adapter, 61 threadably attached to a rotor shaft 15b of the viscosity detection head 33 and the rotor attaching/detaching part, which will be hereinafter called a connection shank, 7d using a magnetic material such as soft steel, fitted to the top end of a rotor stem 7c of the rotor 7.

The connection adapter 61 consists of a shell 61a made of a magnetic material such as soft steel and a permanent magnet 61b contained in the shell 61a. A taper hole 61c is made in the bottom end of the shell 61a so as to become axially aligned with the rotor shaft 15b. Further, the shell 61a and the permanent magnet 61b are fitted without coming into contact with each other so as to produce a gap 61d. The connection shank 7d is formed with a taper face 7e matching the taper hole 61c made in the bottom end face of the connection adapter 61.

In addition to the connection shank 7d, the rotor 7 comprises a flange 7g used when the separation aid mechanism 50 separates the rotor 7, at a position between an immersion liquid mark 7f and the connection shank 7d of the rotor stem 7c.

The separation aid mechanism 50 is a mechanism used when the rotor 7 connected to the detection head 33 is inserted into the rotor magazine mechanism 40 and separated from the detection head 33.

Figure 6A:
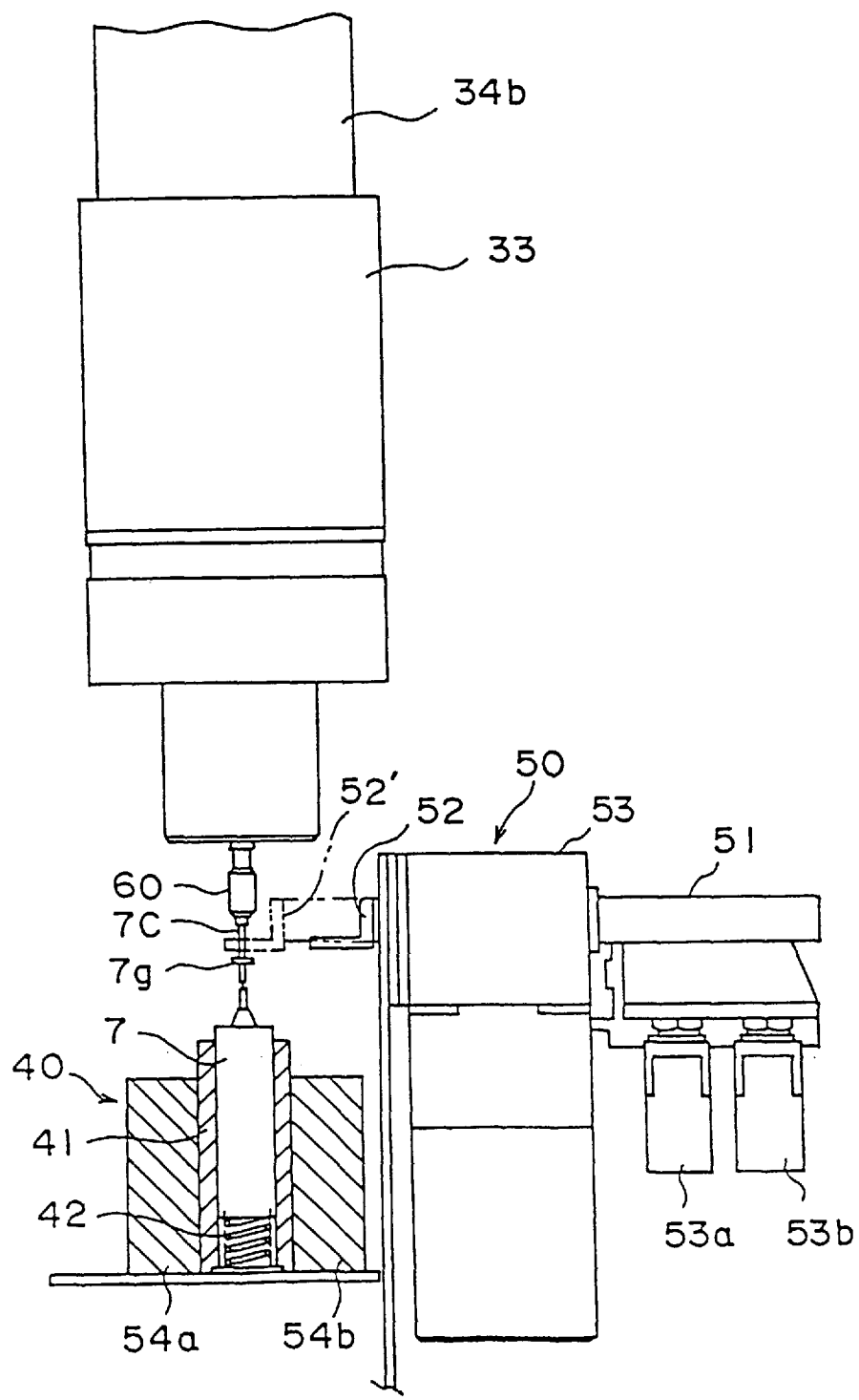
FIG. 6 (a) is a side view of an automatic rotor attaching/detaching system.
Figure 6B:
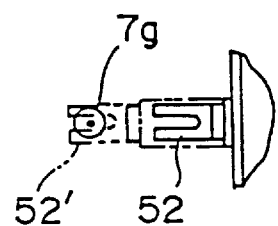

As shown in FIG. 6 (a), the separation aid mechanism 50 has a fork 52 moving to a phantom line position (52') indicated by the alternate long and two short dashes line for sandwiching the rotor stem 7c and extending above the flange 7g, a detaching manipulation arm 51 having a tip to which the fork 52 is fitted, a separation drive 53 for horizontally moving the detaching manipulation arm 51, for example, by electrical driving, and limit switches 53a and 53b for limiting the movement range of the detaching manipulation arm 51. FIG. 6 (b) shows a state in which the positional relationships among the parts in the separation aid mechanism 50 are viewed from above.

The rotor magazine mechanism 40 is a mechanism used for storing a plurality of rotors 7 of the same type or a plurality of rotors 7 of different types to be attached/detached, selecting the next rotor 7 to be used from among them, and positioning the selected rotor 7 at the rotor attaching/detaching manipulation position.

Figure 3A:
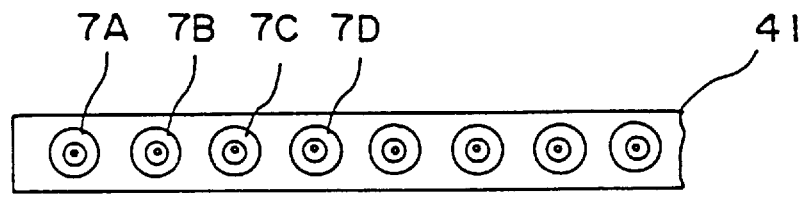
FIG. 3 (a) is a top view of one example of the structure of a rotor magazine.
Figure 3B:
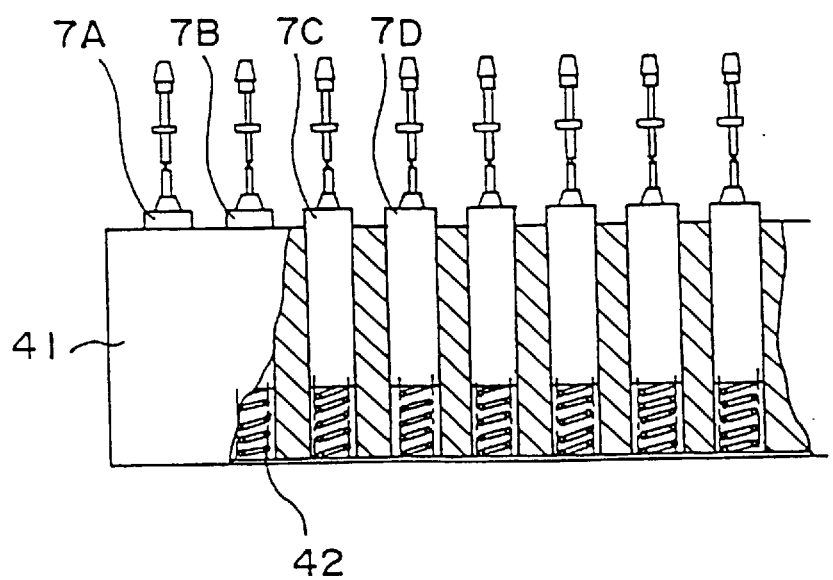
Figure 4:
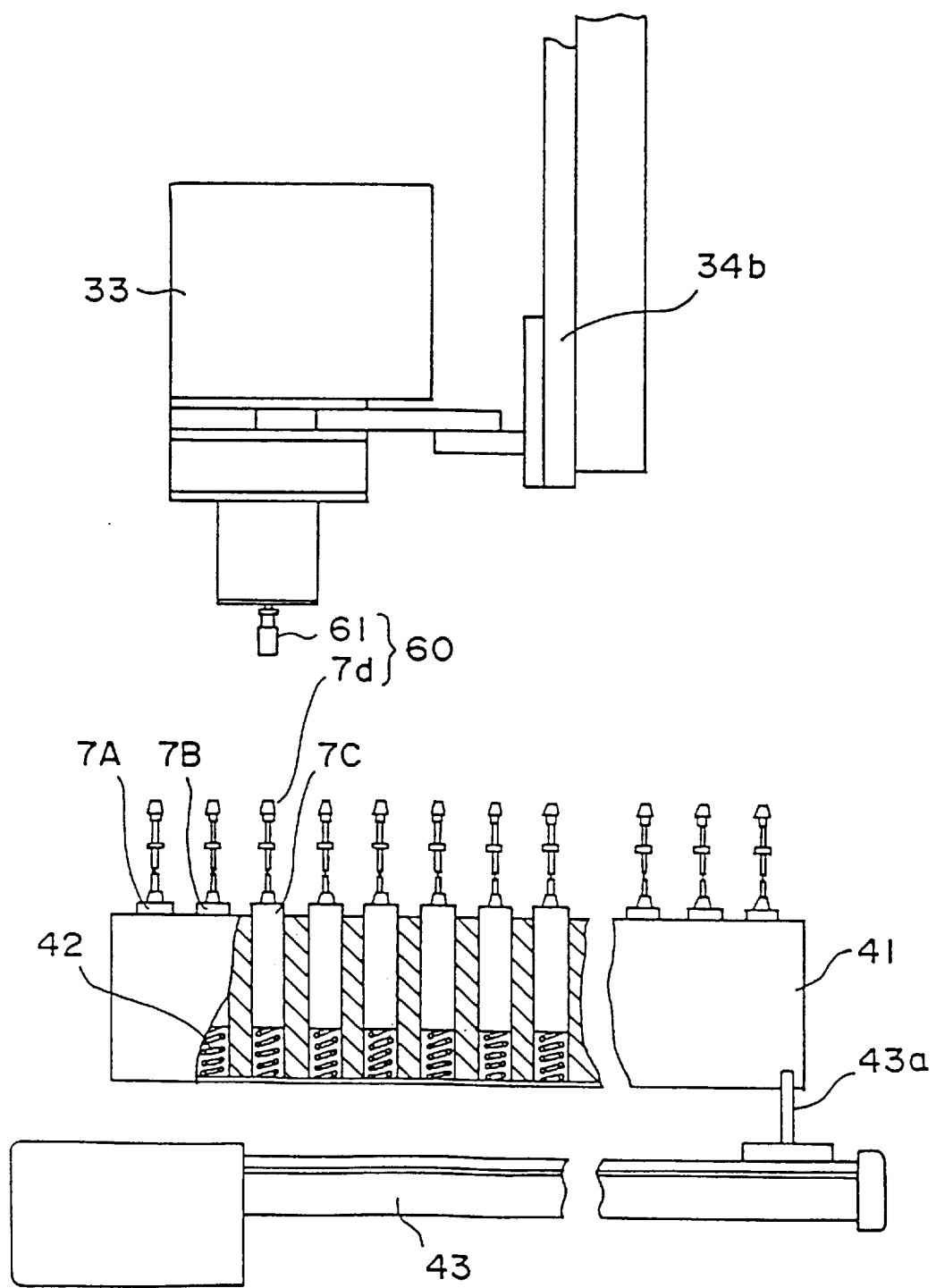
FIG. 4 is an illustration for showing a rotor magazine positioning method.

As shown in FIGS. 3 and 4, the rotor magazine mechanism 40 has a magazine block 41 onto which a plurality of rotors 7 (7A, 7B, 7C, etc.,) are installed and a rotor magazine move mechanism 43 for driving the magazine block 41.

The magazine block 41 is a plastic or metal block formed with holes placed at equal pitches in straight line, as shown in FIG. 3, and a plurality of rotors 7A, 7B, 7C, . . . are inserted into the holes so that their respective rotor steps project. A coil spring 42 is connected to the bottom of each hole for supporting the rotor in a floating state.

Figure 12:
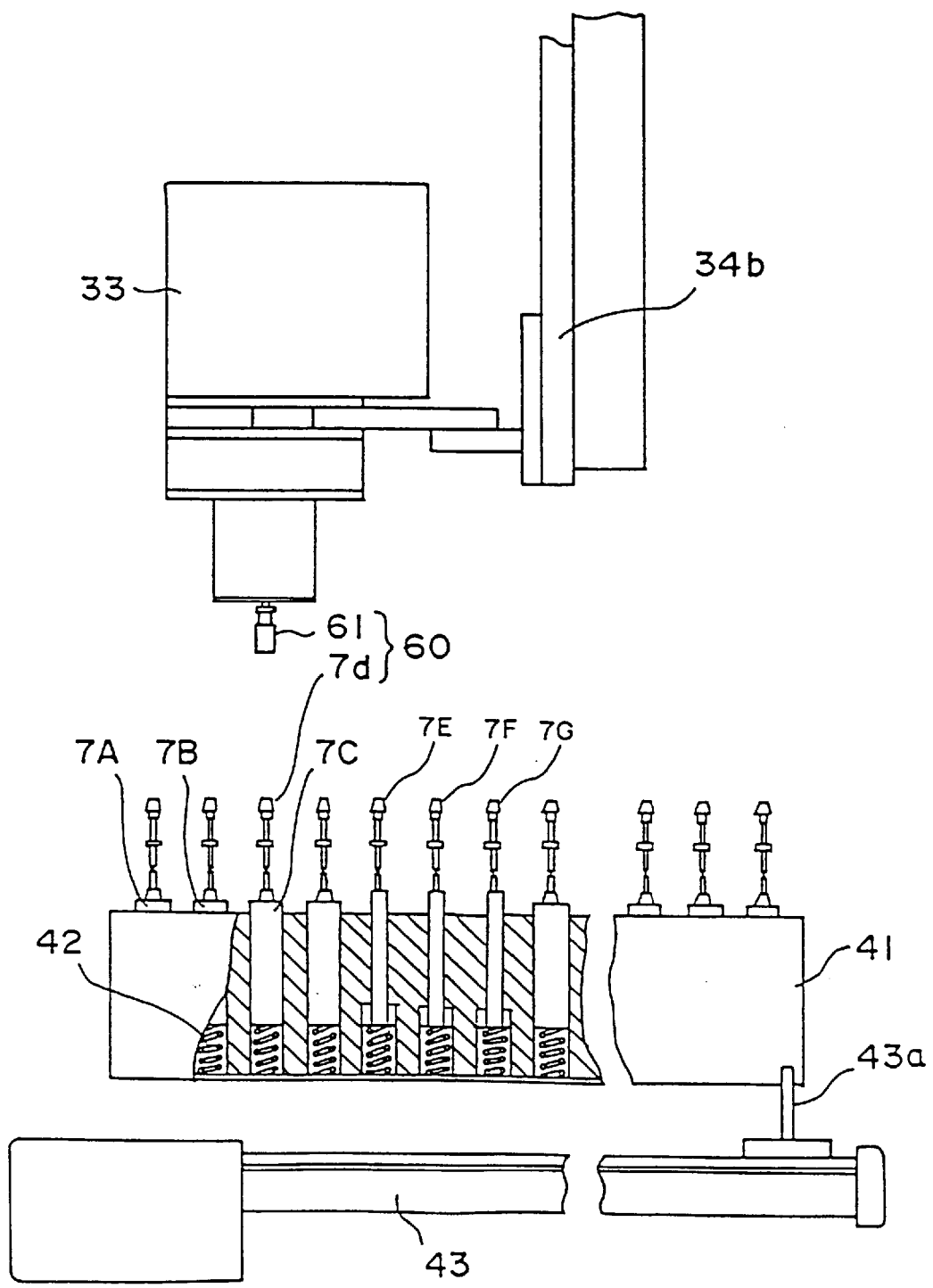
FIG. 12 is an illustration showing another rotor magazine configuration to which the invention is applied.

As shown in FIG. 12, the magazine block 41 may have a structure wherein different-shaped rotors 7A, 7B, 7C, 7E, 7F, 7G, etc., can be installed together. According to the structure, the type of rotor to be used can be selected for replacement with the current rotor for executing automatic measurement so that measurement of specimen liquids of different types can also be covered. For example, a rotor having a large diameter size can be used for low-viscosity specimen liquids and a rotor having a small diameter size can be used for high-viscosity specimen liquids.

According to such structure of the magazine block 41, measurement conditions in an extremely wide range can be selected and large automation advantages can be provided.

If the holes of the magazine block 41 are placed in straight line, for example, as shown in FIG. 4, a motor-driven positioning actuator can be used as the rotor magazine movement mechanism 43 for positioning a rotor at the rotor attaching/detaching manipulation position.

The rotor magazine movement mechanism 43 has an actuator slider 43a for linearly moving the magazine block 41, whereby position control can be facilitated. FIG. 4 shows a state in which the rotor 7C is positioned at the rotor attaching/detaching manipulation position.

As shown in FIG. 6 (a), the magazine block 41 has guide blocks 54a and 54b on side faces.

Figure 13:
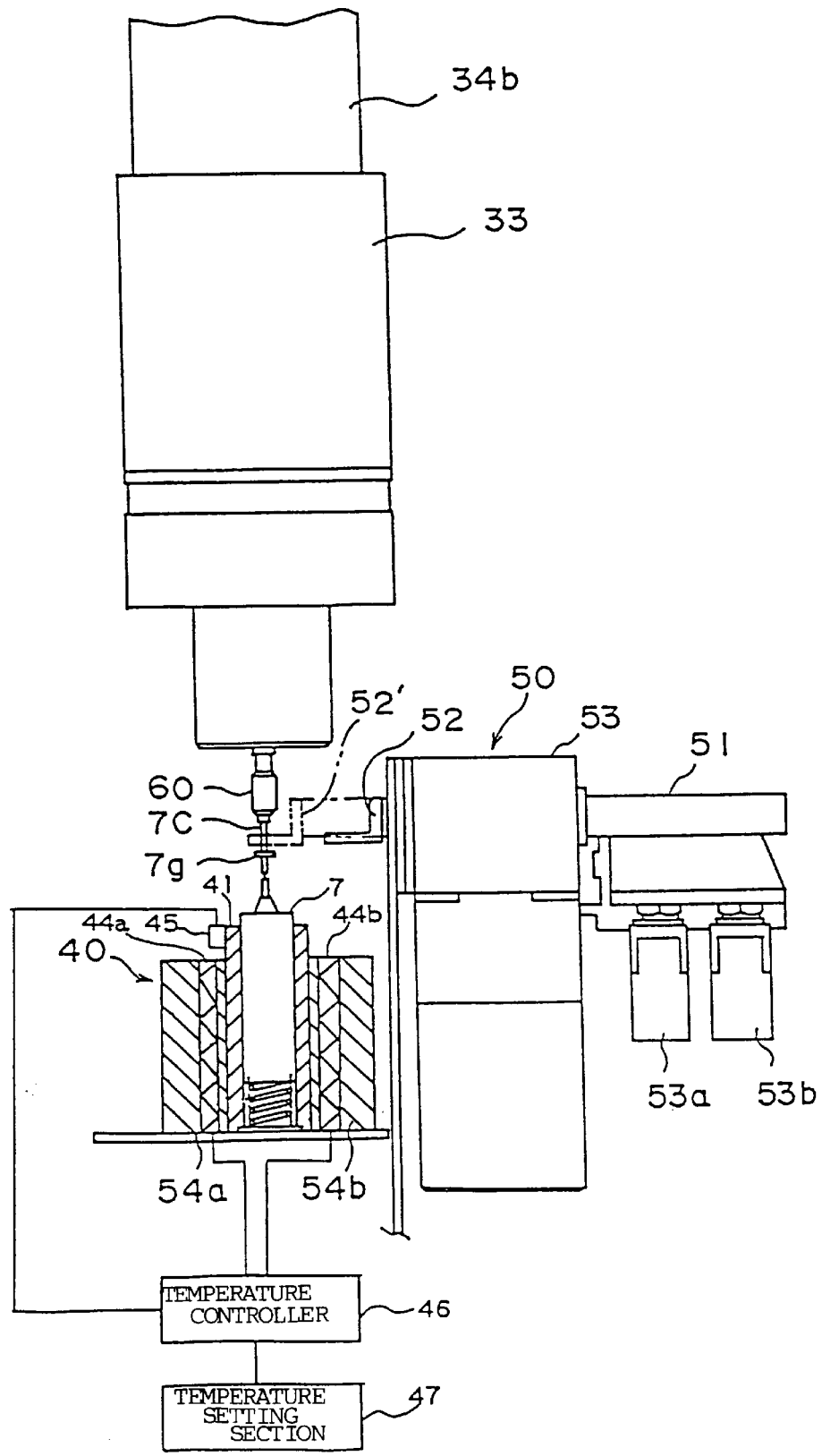
FIG. 13 is an illustration showing another rotor magazine configuration to which the invention is applied.

A temperature adjustment mechanism may also be provided for adjusting the temperature of rotors 7 held in the magazine block 41. For example, to hold the rotors 7 at a temperature higher than the room temperature, the temperature adjustment mechanism comprises heaters 44a and 44b contained in the guide blocks 54a and 54b, a temperature sensor 45 for detecting the temperature of the magazine block 41 as the temperature of the rotors 7, a temperature controller 46 for controlling the heaters 44a and 44b based on the detection result from the temperature sensor 45, and a temperature setting section 47 for setting the holding temperature, as shown in FIG. 13.

Such a temperature adjustment mechanism enables the rotor 7 before viscosity measurement to be held at a predetermined temperature, for example, the same temperature as the specimen liquid to be measured. This can suppress temperature change caused by putting the rotor 7 having a temperature different from the liquid temperature of the specimen liquid into the specimen liquid, further enhancing the reliability of measurement.

The holes of the magazine block 41 are arranged in straight line in the embodiment, but may be arranged like an annular shape or as a plane like intersection points on a two-dimensional grid pattern when viewed from above. In this case, however, the rotor needs to be positioned at the rotor attaching/detaching manipulation position by performing a complicated two-dimensional (X-Y axis) movement operation rather than a one-dimensional movement operation.

As shown in FIG. 7, the viscometer detection head 33 has a rotation drive motor 33A for driving the rotor 7, a torque detection section 33B for detecting a torque by detecting the rotation phase difference between the rotation drive motor 33A and the rotor 7 connected via an elastic member having a predetermined spring constant, and a rotating bearing mechanism with a lock function 33C for connecting the rotation drive motor 33A and the torque detection section 33B and the rotor 7 and when the rotor is attached or detached, locking the rotor shaft for protection.

The viscosity detection head 33 can have the same structure as the mechanical structure used in the viscometer example described in "Rotary viscometer with automatic protector for protecting jewel bearing and pivot" (Japanese Patent Application No. Hei 1-51655 and Japanese Patent Laid-Open No. Hei 2-231549) filed by the present inventor, for example. In this structure, a jewel bearing and pivot come into automatic contact with each other only at the time of viscosity measurement and a torque detection shaft is supported with the jewel bearing, the measurement mode being entered; at the time of non-measurement, rotor shaft rotation is automatically restrained at the same time as the jewel bearing and pivot are separated from each other, thereby automatically protecting the jewel bearing and pivot in association with running of the viscometer.

As shown in FIG. 1, the index turn table unit 30 consists of a turn table rotation mechanism 30A and a turn table 30B rotated by the rotation mechanism 30A. The turn table 30B has a lower part immersed in an annular constant-temperature water bath 32.

Holes are made in the margins of the turn table 30B at equal division positions of the circumference of a circle. Specimen liquid vessels 31A, 31B, 31C, . . . , such as beakers containing sampled specimen liquids, are set into in the holes. Constant temperature water is supplied to the constant-temperature water bath 32 from an external circulation constant-temperature water bath (not shown) for holding the specimen liquid vessels at the constant temperature.

The rotor cleaning unit 35 consists of two cleaning pots 35A and 35B and a cleaning mechanism 35C. The reason why it has two cleaning pots is that, it may be possible to clean the rotor in warm water or it may have to be cleaned in cleaning solvent liquid, depending on the specimen liquid, and that warm water and cleaning solvent liquid need to be used properly. The cleaning mechanism 35C cleans the rotor in warm water or with a solvent with a rotating brush in the cleaning pot. The rotating brush is driven by the cleaning mechanism 35C. The warm water or solvent which has been used is discharged as a drain through a drain pipe connected to the cleaning pot bottom.

The display section 80 displays the calculated viscosity, the current measurement sequence being executed, etc., and is made up of LEDs (light emitting diodes), liquid crystal panels, etc.

The setting section 90 is used to give a measurement start command and set a measurement sequence, etc., and is made up of a keyboard, etc.

As shown in FIG. 7, the control section 200 has a central control circuit 210 for controlling operation sequences of the components and mechanisms described above, a viscosity measurement section 220 for performing processing involved in viscosity measurement, a rotor magazine control circuit 230 for controlling the operation of the components and mechanisms, a turn table control circuit 240, a cleaning mechanism control circuit 250, a detection head moving mechanism control circuit 260, and a separation control circuit 270. Specifically, the control section 200 is made up of a CPU, memory, etc.

The viscosity measurement section 220 has a motor drive circuit 222 for controlling the rotation drive motor 33A, an arithmetic circuit 226 for accepting a signal from the torque detection section 33B and calculating the viscosity, and a viscosity detection head control circuit 224 for controlling the motor drive circuit 222, the arithmetic circuit 226, and the rotation bearing mechanism with a lock function 33C.

Figure 9:
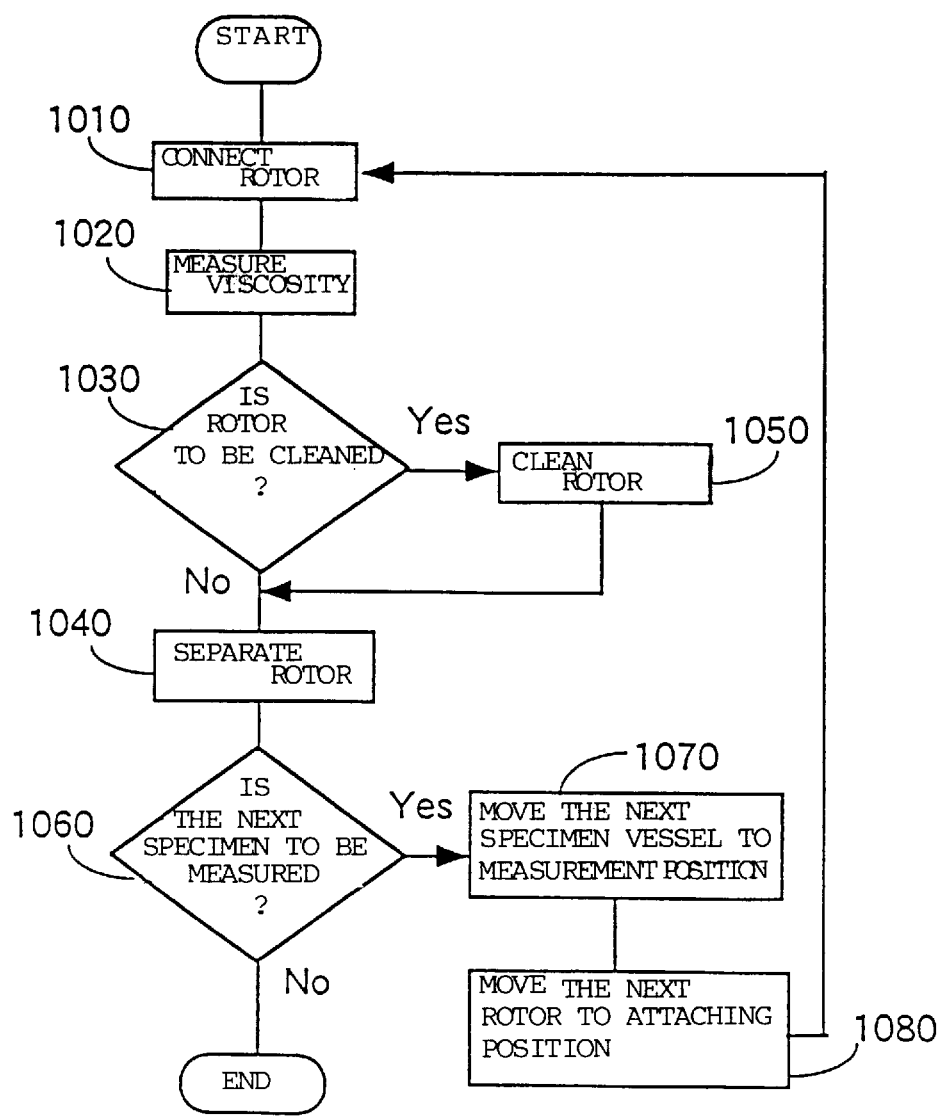
FIG. 9 is a flowchart explaining the operation of the embodiment in FIG. 7.

Next, the operation of the embodiment will be discussed with reference to a flowchart in FIG. 9.

The embodiment assumes that setting related to viscosity measurement, such as the number of revolutions of the rotor 7, and setting related to a measurement sequence, such as specification of the rotor to be used, the number of the specimens to be measured, and whether or not cleaning is to be executed, are carried out through the setting section 90 before measurement.

According to the embodiment, first a rotor 7 is connected to the viscosity detection head 33 at step 1010.

The viscosity detection head 33 and the magazine block 41 are positioned at an attaching/detaching manipulation position by the detection head moving mechanism 34 and the rotor magazine moving mechanism 43 respectively. The attaching/detaching manipulation position is the state, for example, as shown in FIG. 4. It is a state in which the rotor 7C is positioned at the attaching/detaching manipulation position.

In this state, when the vertical elevating actuator 34b operates for moving down the viscosity detection head 33, the connection shank 7d of the rotor 7C is inserted into the taper hole 61c of the connection adapter 61 fitted to the rotor shaft 15b on the bottom end of the viscosity detection head 33 (see FIG. 8).

The connection shank 7d is attracted by the permanent magnet 61b contained in the connection adapter 61, connecting the rotor 7C to the detection head 33. This connection state becomes the state 1 indicated by alternate long and two short dashes lines in FIG. 1. At this time, even if the rotor 7C and the rotor shaft 15b slightly deviate from each other with respect to their axes, the connection shank 7d is guided by the taper face 7e and the taper hole 61c for connecting the rotor 7C and the rotor shaft 15b which are axially aligned.

Figure 10:
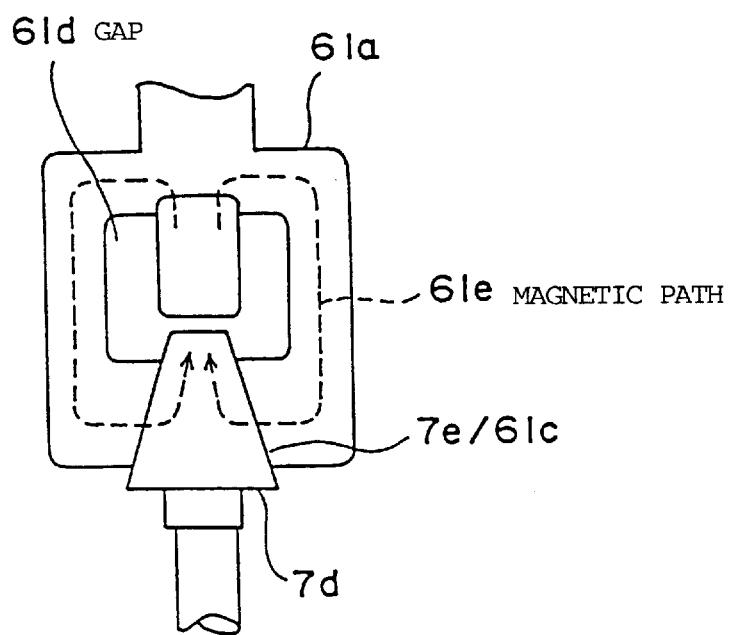
FIG. 10 is an illustration showing a magnetic path defined in the connection part of a rotor and a rotor shaft according to the invention.
Figure 11A:
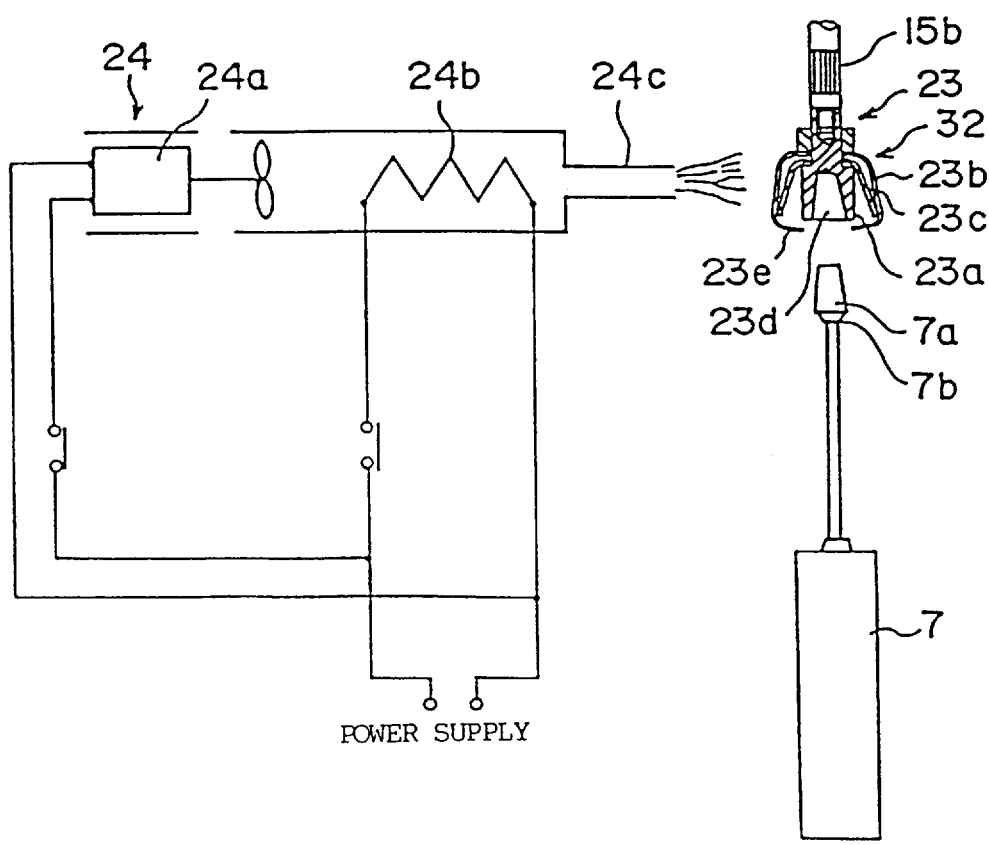
FIG. 11 (a) is an illustration showing a conventional automatic rotor attaching/detaching mechanism.
Figure 11B:
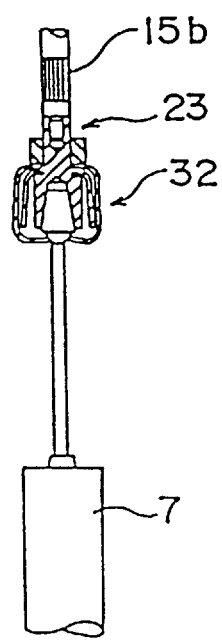

Further, the connection adapter 61 in the embodiment is formed so as to produce the gap 61d between the permanent magnet 61b and the shell 61a. Thus, a magnetic path 61e is defined through the taper face 7e (and the taper hole 61c) in the shell 61a and the connection shank 7d, as shown in FIG. 10. Thus, when the connection shank 7d and the permanent magnet 61b are connected, a vertical magnetic force acts and a magnetic attraction force also acts on the taper face 7e; the rotation torque of the rotor 7 is transmitted to the rotor shaft 15b so as not to cause a rotation difference.

The coil springs 42 attached to the bottoms of the holes in the magazine block 41 (see FIG. 4) support the rotors 7 in a floating state for preventing the internal mechanism of each rotor 7 or the viscosity detection head 33 from being broken if the connection adapter 61 moves down over a predetermined rotor attaching/detaching height, namely, the holding height position of the connection shank 7d when the viscosity detection head 33 moves down.

In the embodiment, the viscosity detection head 33 further includes the bearing mechanism with a lock function, 33C. Thus, when the rotor is connected, if an external force should act, the internal mechanism of the bearing mechanism, etc., is protected.

Next, in the embodiment, viscosity measurement is executed at step 1020. When the rotor 7 is connected at step 1010, the viscosity detection head 33 is moved up by the vertical elevating actuator 34b and is moved to the position 2 shown in FIG. 1 by the horizontal movement actuator 34b. Further, it is moved down by the vertical elevating actuator 34b and the rotor 7 is immersed, to a predetermined position, in the specimen to be measured filled in the beaker 31A, and then viscosity measurement is started.

Upon completion of the viscosity measurement, whether or not the rotor 7 used for the measurement is to be cleaned is determined at step 1030. If cleaning is specified, the rotor 7 is cleaned by the cleaning unit 35 at step 1050. Whether or not cleaning is executed, as well as the cleaning method, are previously determined when a measurement sequence is preset for each specimen. Each specimen beaker may be provided with a bar code indicating information concerning specification of the type of rotor to be used for measurement, measurement conditions such as the number of revolutions of the rotor, and steps after the specimen measurement, such as the cleaning step, and the information may be read at the turn table unit 30.

Next, the detection head 33 is moved to the rotor separation manipulation position as shown in FIG. 6 (a) and the rotor 7 is separated at step 1040.

To separate the rotor 7 connected to the viscosity detection head 33, the detection head 33 is moved by the detection head moving mechanism 34 and the rotor 7 is inserted into an "empty" insertion hole in the magazine block 41. The bearing mechanism 33C of the viscosity detection head 33 is locked to protect the internal structure of the detection head 33. Further, when the connection adapter 61 moves down to the predetermined rotor attaching/detaching height, the bottom face of the rotor 7 compresses the coil spring 42 mounted on the hole bottom in the magazine block 41.

In the state shown in FIG. 6 (a), the detaching manipulation arm 51 of the separation aid mechanism 50 slides from the right, and the fork 52 disposed in the tip extends to the position 52' indicated by the phantom line. FIG. 6 (b) shows the state when the positional relationship is viewed from above. As shown in the figure, the fork 52 sandwiches the rotor stem 7c between two blades of the fork at the position 52' indicated by the phantom line, and extends above the flange 7g.

When the vertical elevating actuator 34b operates to move the viscosity detection head 33 up, the rotor 7 is pressed by the fork 52 of the detaching manipulation arm 51 at the position of the flange 7g, is thus disconnected from the connection adapter 61 and left in the rotor insertion hole in the magazine block 41. After the separation of the rotor 7 ends, the detaching manipulation arm 51 is restored to the former position and the detaching operation of the rotor 7 is now complete. The detaching manipulation arm 51 is positioned by the limit switches 53a and 53b.

The upward movement of the rotor 7 is suppressed using the flange 7g and the fork 52 in the embodiment, but it may be suppressed using other engagement members.

In the separation method of the invention, when the rotor 7 is separated, it is pulled against the attraction force of the permanent magnet 61b (see FIG. 8). The direction of this separation force is axial with respect to the rotor shaft of the viscosity detection head 33. In the embodiment, if such an axial external force acts, the bearing mechanism with a lock function 33C securely restrains the rotor shaft at a portion just above the rotor shaft, so that the internal mechanism of the viscosity detection head 33 containing the torque detection shaft is protected with safety.

Upon completion of the rotor separation, whether or not the next specimen is to be measured is determined at step 1060. This determination is also made based on the preset measurement sequence. If no specimens to be measured exist, the operation is terminated.

If the next specimen to be measured exists, based on the measurement sequence, the specimen beaker containing the specimen to be measured is moved to the measurement position at step 1070 and the rotor 7 used for the next measurement is moved to the rotor connection manipulation position at step 1080. In this state, control returns to step 1010 for connecting the rotor 7 and repeating the above-mentioned measurement operation. Steps 1070 and 1080 may be reversed.

The embodiment uses a magnetic attraction force to attach or detach the detection head 33 and the rotor 7 having the above-mentioned structure and effect. However, the structure to be used for the attaching/detaching part of the invention is not limited to the structure as in the embodiment. Any other attraction force can be used if it does not become an obstacle to the measurement operation with the rotor 7 and the detection head 33.

The embodiment uses horizontal and vertical movements in the detection head moving mechanism 34, but a swivel robot arm mechanism may be adopted.

In the embodiment, the rotor is connected and separated at the same position, but may be done at different positions. For example, an empty rotor magazine for entering rotors after the measurement end may be disposed at a separation position. In such a case, the rotors can be cleaned in batches and the apparatus need not be provided with the cleaning unit.

The embodiment adopts the method using the attraction force of a magnet to directly attract a rotor for connection as a method whereby the rotor can be attached or detached for a short time. The method makes it possible to accomplish the purpose of carrying out an attaching/detaching operation in a short-time, and also to easily attach or detach a rotor to or from the viscosity detection head in association with the movement operation.

The invention enables automatic rotor attaching and detaching in a short time, thus can provide an off-line automatic viscosity measuring apparatus and drastically widen the automation range of viscosity measurement.

We claim:

1. An automatic viscosity measuring apparatus comprising a detachable rotor and a detection head for measuring viscosity of a specimen liquid to be measured with the rotor connected thereto, wherein the improvement comprises:

a detection head moving mechanism for moving said detection head between a connection position at which the rotor is connected to said detection head, a separation position at which the connected rotor is separated from said detection head, and a measurement position at which the viscosity of the specimen liquid is measured;

a rotor holding section being disposed at the connection position for holding one or more rotors in a state in which they can be connected to said detection head; and a rotor movement regulation section being disposed at the separation position for suppressing displacement of the rotor connected to said detection head when the rotor is separated, said rotor having a rotor side attaching/detaching part on a top end, said detection head having a detection head side attaching/detaching part on a bottom part, said rotor side attaching/detaching part and said detection head side attaching/detaching part each having a member on which an attraction force acts mutually, wherein said rotor further includes a flange work part disposed below said rotor side attaching/detaching part, and wherein said rotor movement regulation section has a suppression member engaging the flange work part of said rotor for suppressing upward displacement of said rotor and a suppression member moving section for moving said suppression member to a predetermined position above the flange work part when said rotor is separated.

2. The automatic viscosity measuring apparatus as claimed in claim 1 further including a specimen transport mechanism for holding a plurality of vessels each storing a specimen liquid to be measured, holding the vessels at a constant temperature, and index-transporting the vessels one at a time to said measurement position.

3. The automatic viscosity measuring apparatus as claimed in claim 2 further including a cleaning mechanism for cleaning the rotor connected to said detection head at a predetermined cleaning position, wherein said detection head moving mechanism moves between said cleaning position, said measurement position, said connection position, and said separation position, in a predetermined order.

4. The automatic viscosity measuring apparatus as claimed in claim 1 wherein said rotor holding section holds a plurality of types of rotors, and wherein each of said rotors of said plurality of types has said rotor side attaching/detaching part.

5. The automatic viscosity measuring apparatus as claimed in claim 1 further including a temperature adjustment mechanism comprising a heater and a temperature sensor contained in a guide member coming in contact with said rotor holding section for keeping temperature of said rotors held in said rotor holding section at a predetermined value, said temperature adjustment mechanism for detecting temperature of said guide member as the temperature of said rotors and controlling a calorific power of said heater based on the detection result.

6. The automatic viscosity measuring apparatus as claimed in claim 1 wherein each of said rotor side attaching/detaching part and said detection head side attaching/detaching part are connected to form a configuration wherein a direction of said attraction force is at angle to a direction in which their axial direction.

7. A rotary viscometer comprising a detachable rotor and a detection head for measuring viscosity with the rotor connected thereto, wherein the improvement comprises:

a detection head elevating mechanism for moving said detection head between a connection position at which the rotor is connected to said detection head, a separation position at which the connected rotor is separated from said detection head, and a predetermined initial position;

a rotor holding section being disposed at the connection position for holding one or more rotors in a state in which they can be connected to said detection head; and a rotor movement regulation section being disposed at the separation position for suppressing displacement of the rotor connected to said detection head when the rotor is separated, said rotor having a rotor side attaching/detaching part on a top end, said detection head having a detection head side attaching/detaching part on a bottom part, said rotor side attaching/detaching part and said detection head side attaching/detaching part each having a member on which an attraction force acts mutually, wherein said detection head side attaching/detaching part is formed with a magnetic member as one of the members on which the attraction force acts and said rotor side attaching/detaching part has a top end formed with a connection shank made of soft magnetic metal having a taper, attracted by magnetic member, wherein said detection head side attaching/detaching part further includes a connection adapter made of soft magnetic metal and formed with a taper hole matching a taper face of said connection shank as the other member on which said attraction force acts, and wherein said magnetic member is disposed on a taper hole bottom side of said connection adapter for magnetically attracting said connection shank approaching it for connecting said rotor and said detection head so as to match the taper face of said connection shank with the taper hole of said connection adapter.

8. The rotary viscometer as claimed in claim 7 wherein said connection adapter has a structure wherein it is attracted with said magnetic member at the taper hole bottom, and wherein when said connection shank is connected, a magnetic path through which magnetic lines of force generated by said magnetic member pass, is defined through a portion where both taper faces of said connection adapter and said connection shank come in contact with each other and a magnetic attraction force acts mutually on both the taper faces of said adapter and said shank.

9. The rotary viscometer as claimed in claim 7 wherein said detection head further includes a jewel bearing and pivot protection means operating in association with rotation stop of said rotor connected to said detection head.

10. An automatic rotor attaching/detaching method used with a rotary viscometer comprising a detachable rotor and a detection head for measuring viscosity with the rotor connected thereto, said method comprising the steps of:

providing a rotor side attaching/detaching part with a tapered connection shank disposed on a top end of said rotor, and a detection head side attaching/detaching part with a connection adaptor with a taper hole matching a taper face of said connection shank disposed on a bottom end of said detection head, said rotor side and detection side head attaching/detaching parts each having a member on which an attraction force acts mutually;

making one of said rotor side attaching/detaching part and said detection head side attaching/detaching part approach the other along a direction in which axial directions of both said parts substantially match for connecting both said attaching/detaching parts by the attraction force, thereby connecting said rotor and said detection head; and suppressing displacement of one of said rotor side attaching/detaching part and said detection head side attaching/detaching part in the direction and displacing the other along the direction against the attraction force for separating both said attaching/detaching parts, thereby separating said rotor and said detection head.

11. An automatic viscosity measurement method of an automatic viscosity measuring apparatus comprising a detachable rotor and a detection head for measuring viscosity with the rotor connected thereto, said method comprising the steps of:

providing a rotor side attaching/detaching part with a tapered connection shank disposed on a top end of said rotor and a detection head side attaching/detaching part with a connection adaptor with a taper hole matching a taper face of said connection shank disposed on a bottom end of said detection head, said rotor side and detection head side attaching/detaching parts each having a member on which an attraction force acts mutually;

moving said detection head to one of previously stored rotors, positioned at a predetermined connection position for making them approach each other along an axial direction in which both axial directions of said rotor and said detection head substantially match for connecting both said attaching/detaching parts by the attraction force, thereby-connecting said rotor and said detection head;

moving said detection head to which said rotor is connected to a predetermined viscosity measurement position and measuring viscosity;

after the viscosity measurement is complete, moving said detection head with said rotor connected thereto to a predetermined separation position; and displacing said detection head in the axial direction against the attraction force with displacement of said rotor suppressed in said axial direction for separating both said attaching/detaching parts, thereby separating said rotor and said detection head.

12. The automatic viscosity measurement method as claimed in claim 1 wherein a specimen liquid to be measured is index-transported to the predetermined viscosity measurement position with the liquid held at a constant temperature.

* * * * *